United States Patent [19]

Casper

[11] Patent Number: 4,460,339
[45] Date of Patent: Jul. 17, 1984

[54] DENTURE ANALYZER

[76] Inventor: James A. Casper, 1830 S. 8th Ave., Yuma, Ariz. 85364

[21] Appl. No.: 469,399

[22] Filed: Feb. 24, 1983

[51] Int. Cl.³ ............................................. A61C 9/00
[52] U.S. Cl. .................................... 433/72; 433/214; 33/174 D
[58] Field of Search ................... 433/213, 214, 55, 56, 433/54, 72, 73; 33/174 D, 174 PA, 175

[56] References Cited

U.S. PATENT DOCUMENTS

| | | | |
|---|---|---|---|
| 1,753,965 | 4/1930 | Ralph | 33/174 D |
| 2,014,289 | 9/1935 | Page | 433/72 |
| 3,321,832 | 5/1967 | Weisberg | 433/214 |
| 3,896,551 | 7/1975 | Stuart | 433/214 |
| 4,182,312 | 1/1980 | Mushahac | 433/214 |

*Primary Examiner*—Robert Peshock
*Attorney, Agent, or Firm*—Harvey B. Jacobson

[57] ABSTRACT

A denture analyzing instrument guages landmark points established on existing dentures to record geometrical data associated therewith for transfer to replacement dentures assembled on models spaced from each other by templates conforming to the recorded data. A second instrument adjusted and orientated on the models in accordance with the recorded data, serves as a guide for assembling the replacement dentures.

29 Claims, 15 Drawing Figures

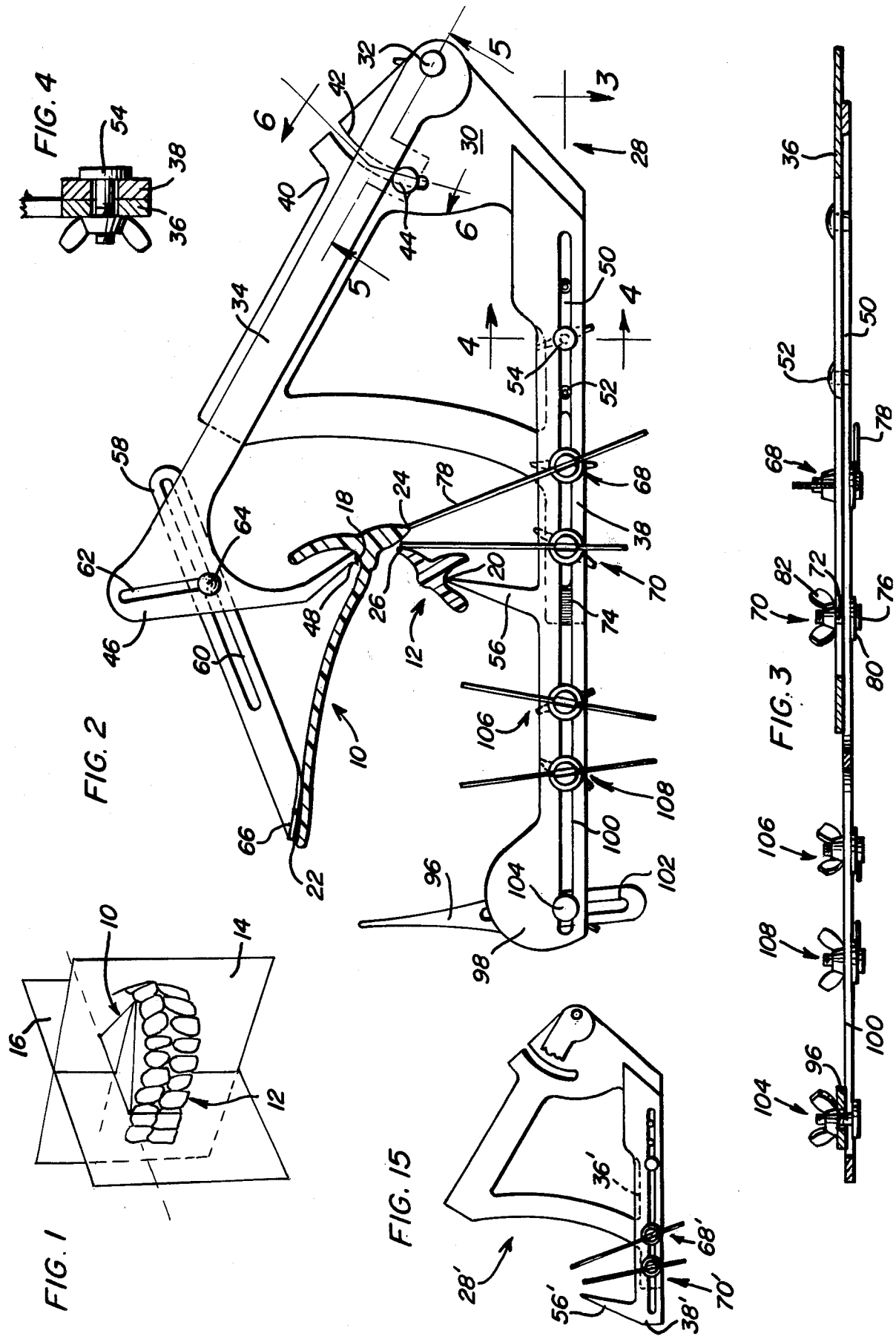

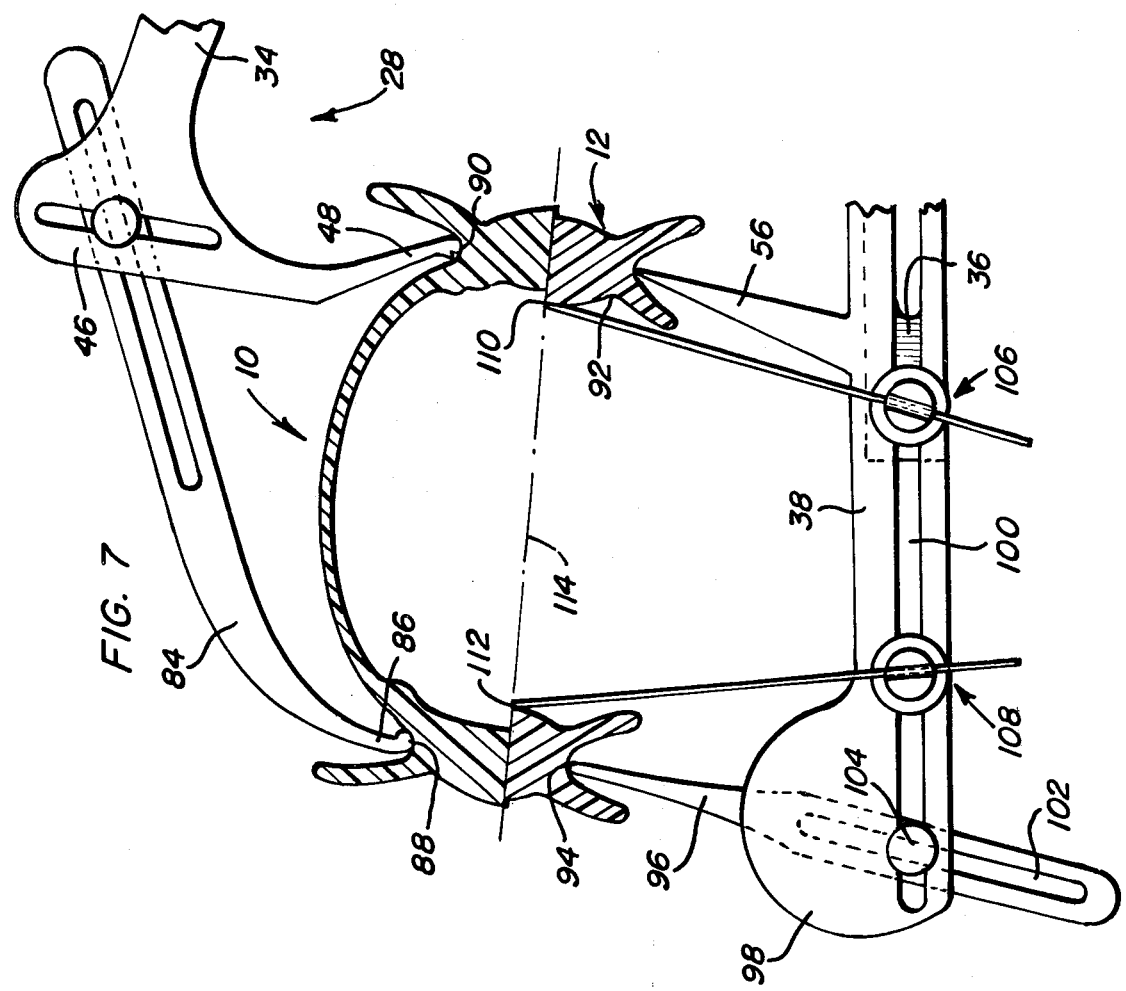
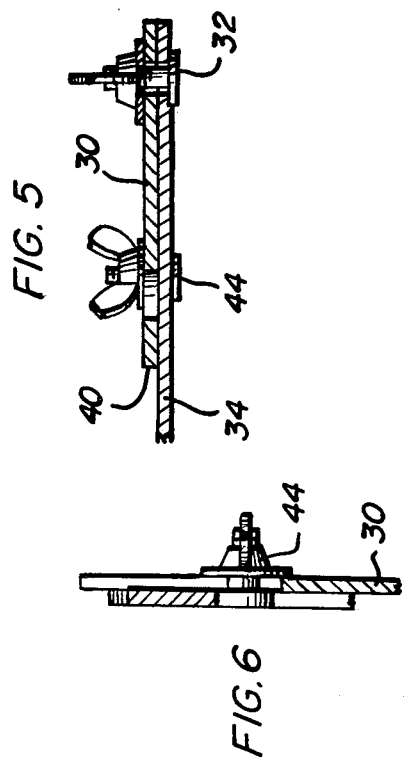
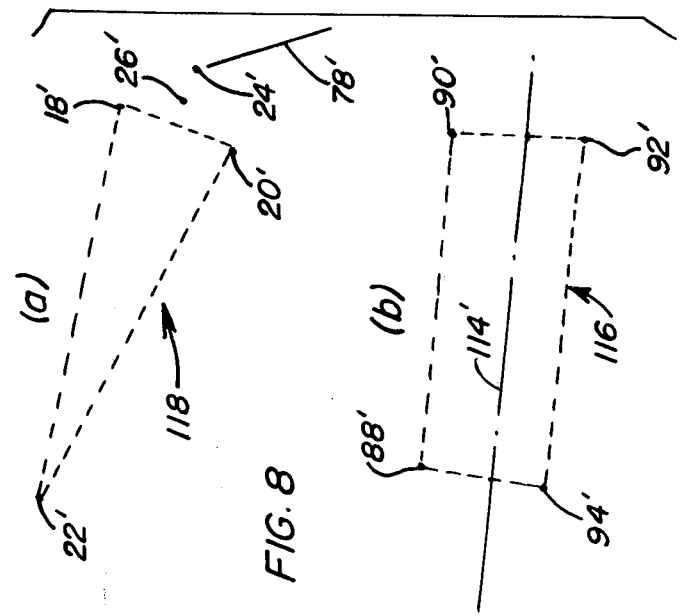

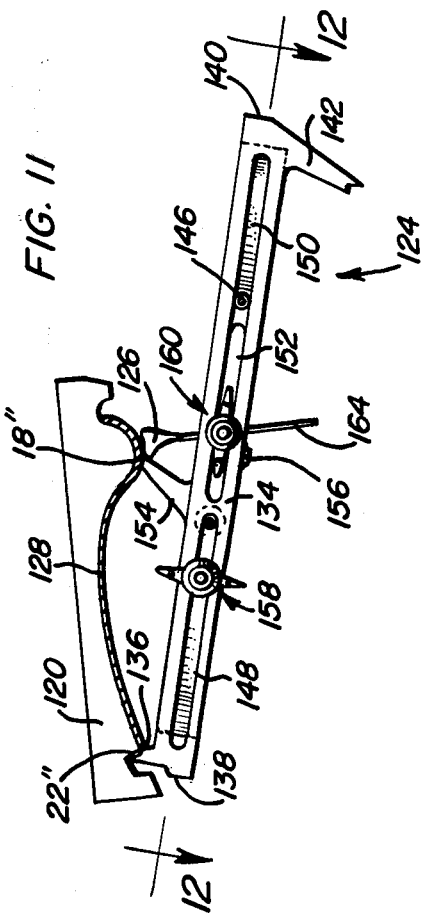
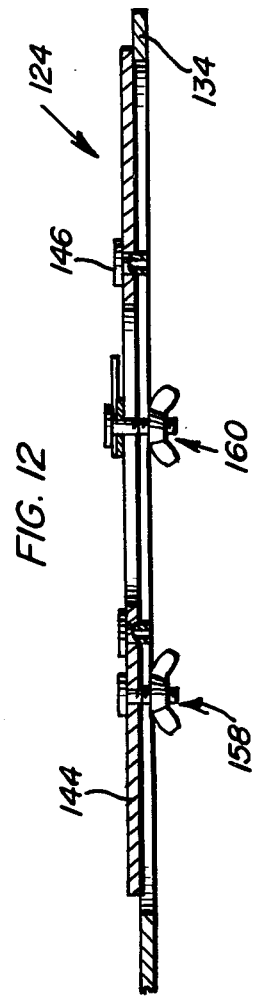
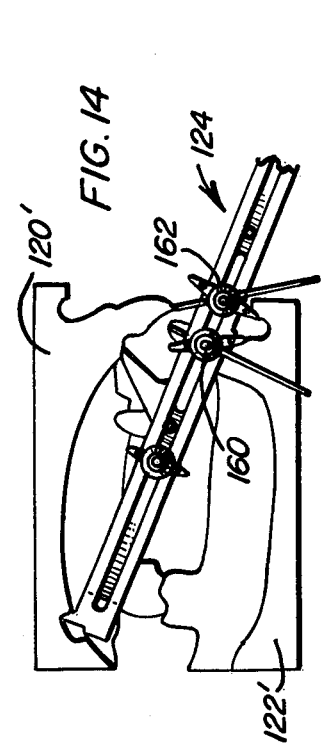
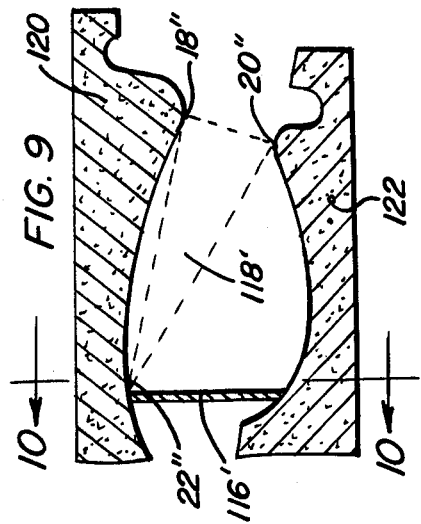
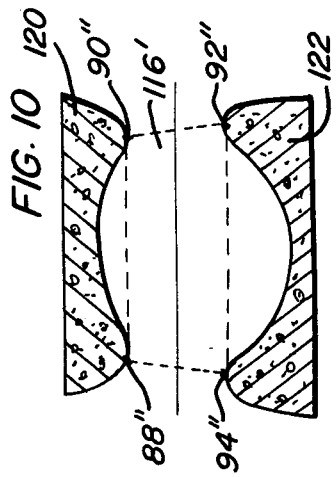
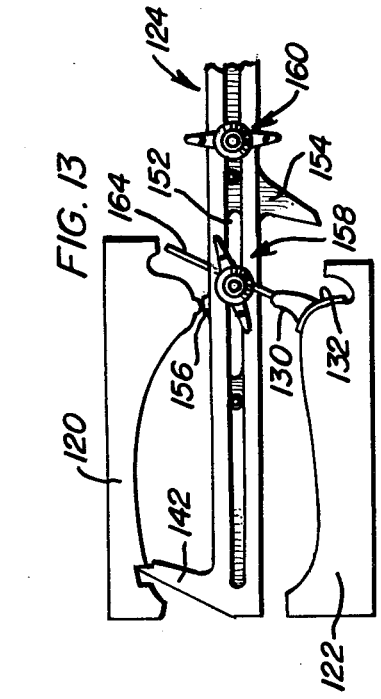

DENTURE ANALYZER

BACKGROUND OF THE INVENTION

This invention relates to a method and apparatus useful in the making of artificial dentures as replacements for old or existing dentures.

Gauging instruments for measuring various geometrical relationships associated with dental prosthesis and human dental anatomy are, of course, well known. Such instruments are useful, for example, in making diagnostic measurements during orthodontic treatment and as guides in the fabrication of artificial dentures. None of such prior art instruments or associated methods are, however, specifically designed to take advantage of experience gained from the immediate past use of existing dentures by a patient as guidance for the fabrication of replacement dentures for the same patient.

It is therefore an important object of the present invention to provide a method and associated instruments through which dental prosthesis may be custom fabricated for a patient in an efficient and accurate manner.

SUMMARY OF THE INVENTION

In accordance with the present invention, a method and apparatus is provided whereby a removable type of dental prosthesis being worn by a patient may be remade or replaced with one to which desirable geometrical features are transferred while undesirable geometrical features are rationally altered or modified. Replacement of both full upper and lower dentures as well as a single full upper or a partial upper may be effected in accordance with the invention. Toward that end, upper and lower dentures while fitted within the patient's oral cavity are adhesively fixed to each other in occlusal relation and then removed from the patient. A plurality of reference points are then established on the interfixed dentures at locations including but not limited to anatomical landmarks such as the incisive papilla, upper and lower ridge crests and the fovea palatina. Such reference points are located in median and frontal planes intersecting each other at right angles. A denture analyzing instrument is then aligned with the median plane and adjusted for contact with the points lying in the median plane in order to measure the geometrical relationships defined by such points. The same denture analyzing instrument is then aligned with the frontal plane and readjusted to contact the dentures at the other points lying in the frontal plane. The measurements made by the denture analyzing instrument with respect to each of the median and frontal planes are recorded on paper or the like from which jaw spacing templates may be made. Models of the upper and lower jaws are then cast and the same reference points located thereon. The templates aforementioned may be utilized to hold the models in spaced relation to each other reproducing the occlusal or biting positions associated with the old existing dentures. Building of replacement dentures may then be initiated by assembly on such models. In order to provide guidance for such assemblage of the replacement dentures, a transfer analyzing instrument is utilized. The transfer analyzing instrument is positioned in contact with the upper jaw model at two of the reference points for orientation thereof. Geometrical data recorded by use of the denture analyzing instrument may then be transferred to adjustable guide elements on the oriented transfer analyzing instrument by means of which artificial teeth such as incisors may be aligned at the proper angles and positions when assembled onto the denture base plate. The transfer analyzing instrument may also be orientated with respect to reference points on interfixed upper and lower study models that are sectioned along the median plane in connection with an "immediate denture" procedure.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view showing interfixed upper and lower dentures intersected by perpendicular median and frontal planes.

FIG. 2 is a section view through interfixed upper and lower dentures in the median plane being measured by a denture analyzing instrument shown in side elevation.

FIG. 3 is a longitudinal section view taken substantially through a plane indicated by section line 3—3 in FIG. 2.

FIG. 4 is an enlarged partial section view taken substantially through a plane indicated by section line 4—4 in FIG. 2.

FIG. 5 is an enlarged partial section view taken substantially through a plane indicated by section lines 5—5 in FIG. 2.

FIG. 6 is an enlarged transverse section view taken substantially through a plane indicated by section line 6—6 in FIG. 2.

FIG. 7 is a section view through the interfixed dentures in the frontal plane being measured by the dental analyzing instrument partially shown in side elevation.

FIGS. 8A and 8B are geometrical diagrams showing the recording of geometrical relationships by the dental analyzing instrument illustrated in FIGS. 2-7.

FIG. 9 is a section view in the median plane through upper and lower jaw models held in spaced relationships to each other by templates.

FIG. 10 is a section view through a frontal plane as indicated by section lines 10—10 in FIG. 9.

FIG. 11 is a section view through an upper jaw model during the fitting of a central incisor on a replacement denture guided by a transfer analyzing instrument shown in side elevation.

FIG. 12 is a section view through the transfer analyzing instrument taken substantially through a plane indicated by section lines 12—12 in FIG. 11.

FIG. 13 is a median plane section view through upper and lower jaw models during the fitting of a lower central incisor guided by the transfer analyzing instrument shown in partial side elevation.

FIG. 14 is a median plane view of upper and lower sectioned study models with the transfer analyzing instrument shown in partial side elevation positioned in contact with the upper model.

FIG. 15 is a side elevational view of a modified form of denture analyzing instrument.

DETAILED DESCRIPTION OF PREFERRED EMBODIMENT

Referring now to the drawings in detail, FIG. 1 illustrates full upper and lower dentures 10 and 12 which have been adhesively interfixed by a sticky wax in occlusal condition while fitted within a patient's mouth. The upper and lower dentures represent an existing or old dental prosthesis which is to be remade or replaced in accordance with the present invention. Also represented in FIG. 1 is a median plane 14 which extends centrally through the incisor portion of the dentures perpendicular to an intersecting frontal plane 16 which extends through the molar portions of the dentures. The interfixing of the upper and lower dentures is accomplished while the molar portions of the dentures are in biting contact at contact points defining an occlusal plane, as is well known in the art.

FIG. 2 illustrates a median plane section through the interfixed upper and lower dentures 10 and 12. In accordance with the present invention, various reference locations are established by marking or the like on the tissue contacting surfaces of the dentures. These reference locations include anatomical landmarks such as the incisive papilla depression at point 18, the crest of the lower anterior ridge at point 20 and the fovea palatina at point 22. Alternatively, reference point 22 may be located on the vibrating line between the hard and soft portions of the upper palate. In cases where fovea palatina or vibrating line is indistinct or unreliable for location of the reference point 22, an arbitrary location in the median plane is utilized since it is only necessary to precisely locate only point 18 in the median plane at the most reliable incisiive papilla landmark. An additional point 24 on the upper denture 10 is located at its incisal or biting edge of the upper central incisor while a point 26 is established on the lower denture 12 at its incisal edge on the lower central incisor.

With continued reference to FIG. 2, a generally planar dental analyzing instrument 28 is shown in engagement with the upper denture 10 at the anatomical landmark points 18 and 22 and the lower denture 12 at point 20 in order to measure or gauge the geometrical relationship associated therewith. The instrument 28 includes a base 30 adapted to be aligned with the median plane as shown in FIG. 2. A pivot member 32 pivotally interconnects the base at a pivot axis with an elongated pivot arm 34. The pivot arm extends from the pivot member 32 over one lateral face of the base for angular displacement in sliding contact therewith. An elongated portion 36 of the base, as more clearly seen in FIG. 3, is adjustably connected to an extensible arm 38 of the instrument. The extensible arm is adjustable along a longitudinal axis in fixed spaced relationship to the pivot axis through pivot 32. The base 30, the pivot arm 34 and the extensible arm 38 constitute major assembled parts of the instrument made of the same rigid sheet material, such as stainless steel.

The pivot arm 34 projects radially from an arcuate edge 40 of the base parallel to an arcuate slot 42 formed therein having a center of curvature at the pivot axis of pivot 32. The slot 42 slidably mounts a stop element 44 that is releaseably locked in an adjusted position by means of a wing nut. The pivot arm arm 34 is engageable with the stop element 44 as shown so as to limit its angular displacement in one direction. The pivot arm 34 has an enlarged end portion 46 opposite the end portion through which the pivot 32 extends. A fixed, rounded (or pointed) tip portion 48 of the pivotal arm projects from the enlarged end portion 46 and is adapted to be received within the incisive papilla depression for contact with the upper denture at landmark point 18.

The extensible arm 38 is provided with a slot 50 through which a pair of rivets 52 extend from the base extension 36 in order to guide longitudinal adjustment of the extensible arm. A wing nut lock 54 extending through the slot 50 releaseably locks the extensible arm in its adjusted position. A fixed tip 56 projects from the extensible arm for contact with the lower denture 12 at point 20 as shown in FIG. 2. It will therefore be apparent that the extensible arm 38 is longitudinally adjusted so as to effect contact between its fixed tip 56 and the lower denture at point 20 while the pivotal arm 34 is angularly adjusted for contact at point 18 on the upper denture with the fixed rounded (or pointed) tip 48. The adjustable stop element 44 may then be locked in position abutting the pivot arm 34 while the extensible arm 38 locked in its longitudinally adjusted position by means of the wing nut lock 54.

The third anatomical reference point 22 in the median plane 14 is gauged by an adjustable tip extension 58 as shown in FIG. 2. The tip extension is accordingly provided with a slot 60 intersecting a slot 62 in the enlarged end portion 46 of the pivot arm. A wing nut lock 64 extends through the intersection of the slots 60 and 62 in order to releasably lock the tip extension 58 in an angular and longitudinal adjusted position relative to the pivot arm 34. One longitudinal end of the tip extension is provided with a contacting flange 66 shown engaging the upper denture at reference point 22 in FIG. 2.

With reference to FIGS. 2 and 3, a pair of angular pointer assemblies 68 and 70 are mounted on the extensible arm 38. Each of the pointer assemblies includes a threaded stem 72 extending through a slot 74 formed in the extensible arm. A flat head 76 is connected to one end of the stem 72 abutting a wire pointer element 78 which extends through an aperture formed in the stem. The wire element is thereby sandwiched between the head 76 and a washer 80 abutting the side face of the extensible arm. A wing nut 82 is threaded onto the stem at the end opposite the head 76 for locking engagement with the extensible arm. Thus, each of the wire elements 78 associated with the adjustable pointer assemblies 68 and 70 may be adjusted along the longitudinal axis of the extensible arm 38, longitudinally adjusted along its own wire axis and angularly adjusted on the extensible arm before being locked in position with the ends of the wire elements contacting the upper and lower dentures at points 24 and 26. The adjusted angular positions of the wire elements 78 provide incisor position and angle guidance as will be explained hereinafter.

With the instrument 28 locked in its adjusted gauging condition as shown in FIG. 2, the pivot arm 34 may be pivotally displaced upwardly from its position engaging the stop 44 so that the instrument then may be withdrawn from the interfixed dentures 10 and 12 without disturbing its fixed condition. Once withdrawn from the dentures, the pivot arm of the instrument is returned to the adjusted position engaging stop 44 and then placed on a surface backed sheet of paper or recording material. The points gauged by the instrument at fixed tips 48 and 56, on flange 66 and at the upper ends of the wire elements 78 may then be transferred to the recording sheet of paper by any suitable marking method to record point 18', 20' and 22' corresponding to the reference points 18, 20 and 22 as shown in FIG. 8A. The additional points 24' and 26' are also recorded together with the incisor angle line 78'.

After the geometrical data gauged by the instrument is recorded, as indicated with respect to FIG. 8A, the instrument is readjusted and aligned with the frontal plane 16 as illustrated in FIG. 7 for gauging the interfixed dentures. Readjustment of the instrument involves replacement of the adjustable tip extension 58 with another tip extension 84 which has a curved end portion 86 engageable with an anatomical reference point 88 on the upper denture in the upper ridge depression. The fixed tip 48 of the pivot arm 34 on the other hand, engages the upper denture at point 90 in the upper ridge depression. The lower ridge crest locations on the lower denture 12 are engaged by the fixed tip 56 of the extensible arm 38 at point 92 and at point 94 by an adjustable tip member 96. The tip member 96 is both angularly and longitudinally adjustable on the extensible arm 38 at the enlarged distal end portion 98. Thus, another slot 100 is formed in the extensible arm intersecting a slot 102 formed in the adjustable tip member 96. A releasable wing nut lock 104 extends through the intersection of the slots 100 and 102. Also, a pair of angularly adjustable pointer assemblies 106 and 108 are mounted on the extensible arm 38 for adjustment along slot 100. The adjustable pointer assemblies 106 and 108 are similar in construction to the adjustable pointer assemblies 68 and 70 hereinbefore described with respect to FIG. 2. The wire elements associated with the pointer assemblies 106 and 108 are adapted to be adjusted for contact at their ends with the lower denture 12 and at lingual surface points 110 and 112 in the occlusal plane 114 as shown in FIG. 7.

Once the reference points 88, 90, 92 and 94 and additional points 110 and 112 are gauged by the instrument 28 in the frontal plane, the instrument is removed and a recording made as shown in FIG. 8B. The recorded reference points 88', 90', 92' and 94' define a quadrilateral 116. The recorded points 110' and 112' on the other hand, define the intersection 114' of the occlusal plane 114 with the frontal plane 16. The recorded points 18', 20' and 22' as shown in FIG. 8A, define a triangle 118. Spacing templates 118' and 116' conforming to the triangle 118 and quadralateral 116 are then made for use as shown in FIGS. 9 and 10.

FIGS. 9 and 10 show upper and lower jaw models 120 and 122 that are cast from the upper and lower impressions taken from the oral cavity of the patient after removal of the old dentures. The upper and lower models 120 and 122 may then be utilized for the making of the replacement dentures. Such upper and lower models are therefore mounted in an articulator in a manner well known in the art but spaced from each other by the spacing templates 118' and 116' as shown in FIGS. 9 and 10. Accordingly, corresponding reference points 18", 20", 22", 88", 90", 92" and 94" are established or marked on the upper and lower models at which the templates contact the models.

The models 120 and 122 of the upper and lower jaws may be utilized in conjunction with a transfer analyzing instrument 124 as shown in FIGS. 11 and 12 to assemble a denture being made to replace the old or existing dentures gauged by the instrument 28 as described with respect to FIGS. 2 and 3. Thus, FIG. 11 shows the transfer analyzing instrument 124 angularly positioned with respect to the upper jaw model 120 for fitting an artificial upper central incisor 126 onto an upper record base 128 placed over the tissue bearing surface reproduced on the model. FIG. 13 on the other hand, shows a different angularly position of the transfer analyzing instrument 124 on the upper model 120 for fitting an artificial lower central incisor 130 on a lower record base 132 over the lower anterior ridge crest of the lower model 122, the lower model being operatively spaced from the upper model by means of the templates 118' and 116' as described with respect to FIGS. 9 and 10.

With reference to FIGS. 11 and 12, the transfer analyzing instrument 124 includes an elongated support member 134 from which a relatively short and recessed anchoring formation 136 projects in one lateral direction adjacent one longitudinal end 138. From the other longitudinal end 140 of the support member, a longer recessed anchoring formation 142 projects in a lateral direction opposite to that of the anchoring projection 136. An elongated adjustment member 144 is slideably connected to the support member 134 through a pair of rivets 146 extending into guide slots 148 and 150 formed in the support member 134 in longitudinal spaced relationship to an intermediate guide slot 152. A model contacting tip 154 projects laterally from the elongated adjustment member 144 in the same lateral direction as the short anchoring formation 136 while a relatively short tip 156 projects from the adjustment member 144 in the opposite lateral direction. The elongated support member 134 and adjustment member 144 are locked in a longitudinally adjusted position by means of a nut locking assembly 158 extending through the guide slot 148. Wing nut locking assemblies 160 and 162 extend through the other slots 152 and 150. Wire guide elements 164 may be adjustably positioned in each of the releaseably locked assemblies 160 and 162 which are similar in construction to the adjustable pointer assemblies 68 and 70 hereinbefore described with respect to the instrument 28.

As shown in FIG. 11, the denture base 128 on the upper jaw model 120 is cut away to expose the reference points 18" and 22" for engagement by the anchoring formation 136 and the tip 154. The longitudinal position of the tip 154 is therefore adjusted for this purpose after which it is locked in position by means of the wing nut associated with assembly 158. The elongated support member 134 will then be in a predetermined angular position properly oriented for transferring the geometrical data gauged by the instrument 28 as hereinbefore described. More specifically, the wire guide element 164 associated with the assembly 160 is adjusted to reproduce the incisor guide angle of the wire pointer element 78 and point 24 at its end on the instrument 28 from the recordings 78' and 24' as shown in FIG. 8A. The artificial central incisor 126 may then be set as shown in FIG. 11 for attachment to the denture base 128 either at the same angle and position as the central incisor associated with the old denture or at a modified angle and position. The adjusted angular position and projecting length of the wire guide element 164 will in any event provide guidance for such assemblage of the new upper denture.

The same wire guide element 164 may be adjusted and locked in adjusted position for guidance in fitting the lower artificial central incisor 130 as shown in FIG. 13. Adjustment of the wire guide element 164 for this purpose is made with respect to a different position of the support member 134 determined by the long anchoring formation 142 and the short tip 156 as shown in FIG. 13.

FIG. 14 shows sectioned study models 120' and 122' of a patient's oral cavity with natural teeth present. Such models were cast and positioned in occlusal relation to each other from which measurements of natural positions may be made with respect to the central incisors and vertical dimension of occlusion. The transfer analyzing instrument 124 is angularly positioned by contact with the upper model 120' at two reference locations corresponding to the reference points 18 and 22 hereinbefore described with respect to FIG. 2. As an alternative to pre-extraction point 18, a more enduring reference point in the median plane could be used. The geometrical data relating to incisal angle and incisal edge positions are set on the adjustable assemblies 160 and 162 corresponding to the angle and incisal edge positions of the upper and lower central incisors cast in the sectioned models 120' and 122' for study purposes. The incisor angles and incisor edges set on the instrument 124 may then be utilized either without or with modification to guide assemblies of an immediate denture or an immediate replacement denture as hereinbefore described with respect to FIGS. 11 and 13.

It will be apparent from the foregoing description that the denture analyzing instrument 28 may be utilized for making various median plane measurements furnishing geometrical data associated with old existing dentures including for example, the vertical dimension of occlusion to which the patient has been accustomed, the position and angle of the upper central incisor, the position of the lower central incisor and possibly its estimated angle, the amount of overjet and overbite, anterior incisal guidance from the angular relationship between points 24 and 26, and the anterior ridge relationship of the upper and lower jaws. With respect to the frontal plane, instrument 28 will provide geometrical data including the positon of four posterior ridge crests in relation to each other in the frontal plane, the amount of posterior interridge space available for teeth, the upper and lower posterior ridge crest relationship, the height of the occlusal plane 114 as depicted in FIG. 7, the relationship of the longitudinal position of the lower molars to the corresponding lower ridge crests, and the amount of tongue space. Permanent records of the foregoing geometrical data may be made from the instrument 28 and templates also made from the recorded data for mounting upper and lower models in the same relationship as the patient's upper and lower denture bearing areas with respect to the old prosthesis. The transfer analyzing instrument 124 provides both transfer and analyzing functions. The transfer functions include guidance in the fitting of the new upper and lower central incisors at predetermined positions and incisal angles during the making of the new prosthesis. The analyzing functions include determining with reference to anatomical features of the patient the upper and lower central incisor locations on the study models 120' and 122' and vertical occlusal dimensions. Use of the transfer analyzing instrument may also be associated with the procedure for making of "immediate dentures" wherein the teeth are left in place in the patient's mouth to make the study models and are removed immediately before insertion of the dentures. The permanent records made of the incisor positions and vertical dimension of occlusion from the study models, in accordance with the present invention, enhances not only the making of immediate dentures but also the subsequent making of new dentures that the patient may require.

FIG. 15 shows a modified form of denture analyzing instrument 28' similar to instrument 28 shown in FIG. 2. Instrument 28', however, has a lower extensible arm 38' that does not extend beyond fixed tip 56'. Proximal wire pointer assemblies 68' and 70' are provided for locating incisor teeth. Such an instrument would be limited in use to median plane measurement of old dentures. Without the pointer assemblies, the instrument would be largely limited to measuring the vertical dimension of occlusion of a patient's old dentures.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. For use in analyzing reference points intersected by median and frontal planes extending through upper and lower dentures fixed in occlusal relationship to each other, a denture analyzing instrument comprising a planar base adapted to be aligned with said median and frontal planes, a pivot mounted on the base, a pivot arm pivotally connected by said pivot to the base, an extensible arm having a longitudinal axis, means mounting the extensible arm on the base for adjustment along said longitudinal axis, fixed tips respectively projecting from the base and the extensible arm, means for releasably locking said arms on the base in adjusted positions wherein the fixed tips respectively contact the upper and lower dentures at two of said reference points in the median plane and adjustable tip extension means mounted on the pivotal arm for contact with a third of the reference points on the upper denture in said median plane, said three of the reference points defining a denture spacing triangle.

2. The instrument as defined in claim 1 including angularly adjustable pointer means mounted on the extensible arm for contact with dentures at points external to said denture spacing triangle in the median plane.

3. The instrument as defined in claim 2 including angularly adjustable tip means mounted on the extensible arm for contact with another of the landmark points lying in the frontal plane.

4. The instrument as defined in claim 3 wherein said angularly adjustable point means includes at least two guide elements adjustable to incisor angle positions in said medium plane, and at least two molar contact elements adjustable to positions in the frontal plane defining an occlusal intersection with the frontal plane.

5. The instrument as defined in claim 2 wherein said angularly adjustable pointer means includes at least two guide elements adjustable to incisor angle positions in said median plane, and at least two molar contact elements adjustable to positions in the frontal plane defining an occlusal intersection with the frontal plane.

6. The instrument as defined in claim 1 including angularly adjustable tip means mounted on the extensible arm for contact with the lower denture in the frontal plane.

7. The instrument as defined in claim 6 wherein the fixed tips, the adjustable tip extension means and the angularly adjustable tip means contact reference points lying in the frontal plane to define a denture spacing quadrilateral.

8. For use on a model of an upper jaw having spaced reference locations established thereon, a transfer guide instrument comprising an elongated support, a pair of anchoring formations projecting by different distances in opposite directions from the support adjacent opposite ends thereof, a pair of contacting tips projecting in opposite directions from the support by different amounts, means adjustably positioning said tips intermediate the formations for engagement of the model at said spaced reference locations by one of the anchoring formations and one of the tips to alternatively orientate the support at two different positions on the model, and adjustable pointer means mounted on the support for respectively establishing upper and lower incisor angle guides in the two different positions of the support.

9. For use on a dental model of an upper jaw having spaced reference locations established thereon, a transfer guide instrument comprising an elongated support, formation means projecting from the support for anchoring thereof at one of the reference locations on the model, a contacting tip projecting from the support in spaced relation to said anchoring formation means, means adjustably positioning the tip on the support for engagement of the model at another of said spaced reference locations to hold the support in a predetermined orientated position relative to the model, and adjustable pointer means mounted on the support for establishing an incisor guide angle in said orientated position of the support.

10. The instrument as defined in claim 9 wherein said adjustable pointer means includes a pair of pointer elements extending at different angles from the support to respectively form upper and lower incisor angle guides.

11. The instrument as defined in claim 9 including a second tip projecting from the support and engageable with the model at said other of the landmark locations to hold the support in another orientated position relative to the model, said adjustable pointer means respectively establishing the incisor guide angle in the two orientated positions of the support.

12. In combination with a pair of instruments, a method of utilizing said instruments to gauge and transfer geometrical relationships of existing upper and lower dentures fixed to each other in occlusal relation for guidance in making a replacement denture, including the steps of: establishing a plurality of reference points on the existing dentures; gauging the geometrical relationships by contacting said established points with one of the pair of instruments; recording said geometrical relationships gauged by said one of the instruments; preparing a model of at least one jaw on which one of the existing dentures fits; marking at least two points on said model corresponding to those on said one of the existing dentures; transferring the recorded geometrical relationships to the other of the pair of instruments; and orientating said other of the instruments by contact with the model at said two points thereon to form an alignment guide for assemblage of a replacement denture on the model.

13. In a method of making a replacement for existing dental prosthesis, including the steps of: adhesively fixing the existing prosthesis in occlusal condition along an occlusal plane while fitted on a patient; establishing a plurality of reference points on the fixed existing prosthesis in at least two intersecting planes; gauging the established reference points on the existing prosthesis to produce geometrical data; preparing an upper jaw model corresponding to said existing prosthesis on which at least an anatomical landmark is located corresponding to one of the reference points; and transferring said geometrical data to the model orientated with respect to said anatomical landmark for guiding assemblage of the replacement prosthesis thereon.

14. The method of claim 13 including the steps of: preparing a second model of the lower jaw; preparing model spacing templates from the geometrical data; assembling the templates and the models in spaced relation to each other; fixing said models in said spaced relationship; and transferring the geometrical data to said second model oriented with respect to said anatomical landmark located on the upper jaw model.

15. The method of claim 14 wherein said anatomical landmark is the incisive papilla on the upper jaw.

16. The method of claim 15 wherein said other of the reference points correspond to additional anatomical landmarks which include molar ridge crests on the upper and lower jaws and a lower anterior ridge crest on the lower jaw.

17. The method of claim 16 wherein additional reference points are established in one of the intersecting planes at incisal edges of the fixed prosthesis.

18. The method of claim 17 wherein said one of the intersecting planes is a median plane through central incisor locations on the existing prosthesis and the other of the said planes is a frontal plane through molar locations on the existing prosthesis.

19. The method of claim 18 wherein the geometrical data includes central incisor angles of the existing prosthesis and the intersection of the occlusal and frontal planes.

20. The method of claim 19 wherein the assemblage of the replacement prosthesis includes fitting of a denture base on each of the models and alignment of artificial central incisors with said incisor angles in preparation for attachment of the artificial central incisors to the denture bases.

21. The method of claim 15 wherein additional reference points are established in one of the intersecting planes at incisal edges of the existing prosthesis.

22. The method of claim 21 wherein the geometrical data includes central incisor angles of the existing prosthesis and the intersection of the occlusal and frontal planes.

23. The method of claim 22 including the step of sectioning the interfixed models along said one of the intersecting planes for study purposes.

24. The method of claim 13 wherein the geometrical data includes central incisor angles of the existing prosthesis and the intersection of the occlusal plane with one of the intersecting planes.

25. The method of claim 24 wherein the assemblage of the replacement prosthesis includes fitting of a denture base on each of the models and alignment of artificial central incisors with said incisor angles in preparation for attachment of the central incisors to the denture bases.

26. The method of claim 14 wherein said templates conform to closed geometrical figures defined by the established points in said intersecting planes.

27. The method of claim 13 wherein one of said anatomical landmark is the incisive papilla on the upper jaw.

28. The method of claim 27 wherein additional reference points are established in one of the intersecting planes at incisal edges of the existing prosthesis.

29. The method of claim 28 wherein the geometrical data includes central incisor angles of the existing prosthesis.

* * * * *